(12) United States Patent
Bachman et al.

(10) Patent No.: US 8,617,143 B2
(45) Date of Patent: Dec. 31, 2013

(54) THERAPEUTIC AGENT DELIVERY SYSTEMS AND DEVICES

(75) Inventors: Mark Bachman, Irvine, CA (US); Baruch Kuppermann, Laguna Beach, CA (US); Asheesh Divetia, Irvine, CA (US); Guann Pyng Li, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1222 days.

(21) Appl. No.: 11/952,626

(22) Filed: Dec. 7, 2007

(65) Prior Publication Data

US 2008/0177153 A1 Jul. 24, 2008

Related U.S. Application Data

(60) Provisional application No. 60/873,795, filed on Dec. 7, 2006.

(51) Int. Cl.
*A61K 9/22* (2006.01)

(52) U.S. Cl.
USPC ...................................... 604/892.1; 424/424

(58) Field of Classification Search
USPC ........ 604/85, 93.01, 294, 304, 306, 514–517, 604/890.1, 892.1; 424/422–437, 484–488
See application file for complete search history.

(56) References Cited

U.S. PATENT DOCUMENTS

| | | | |
|---|---|---|---|
| 7,141,429 B2 | 11/2006 | Munson et al. | |
| 7,621,907 B2 * | 11/2009 | Rodstrom | 604/892.1 |
| 7,947,491 B2 | 5/2011 | Jeon et al. | |
| 2003/0176854 A1* | 9/2003 | Rodstrom | 604/891.1 |
| 2004/0034332 A1* | 2/2004 | Uhland | 604/500 |
| 2004/0106129 A1 | 6/2004 | Crook et al. | |
| 2004/0121066 A1 | 6/2004 | Anderson et al. | |
| 2004/0243106 A1* | 12/2004 | Ayer | 604/892.1 |
| 2005/0107772 A1* | 5/2005 | Chen et al. | 604/892.1 |
| 2005/0217750 A1 | 10/2005 | Jeon et al. | |
| 2005/0266582 A1 | 12/2005 | Modlin et al. | |
| 2007/0178582 A1 | 8/2007 | Koser | |
| 2007/0250046 A1* | 10/2007 | Trieu | 604/892.1 |
| 2008/0014575 A1 | 1/2008 | Nelson | |
| 2011/0003372 A1 | 1/2011 | Jeon et al. | |

OTHER PUBLICATIONS

Duffy et al. Rapid prototyping of microfluidic systems in poly(dimethylsiloxane). Analytical Chem. (1998). 70(23): 4974-4984.

U.S. Appl. No. 11/849,194 Notice of Allowance dated Jan. 20, 2011.

* cited by examiner

*Primary Examiner* — Kami A Bosworth
(74) *Attorney, Agent, or Firm* — Sean D. Senn; Nixon Peabody LLP

(57) ABSTRACT

Devices, systems and methods for delivering pre-determined quantities of an active ingredient to a biological system are provided. In various embodiments, a device for controlled release of an active ingredient is provided, including a release aperture operably associated with a deflectable member, a base with a porous membrane substrate layer, and at least one chamber juxtaposed between the release aperture and the porous membrane layer. The chamber may contain a matrix including one or more active ingredients and an agent that expands when contacted with an aqueous solution. The device is suitable for implantation in a biological system and can be used for delayed and/or time release of specific drug dosages for various indications.

11 Claims, 9 Drawing Sheets

27
THERAPEUTIC AGENT DELIVERY SYSTEMS AND DEVICES

CROSS REFERENCE TO RELATED APPLICATIONS

For purposes of the USPTO extra-statutory requirements, the present application claims priority to U.S. Provisional Application Ser. No. 60/873,795 filed Dec. 7, 2006. Accordingly, this application claims benefits under 35 USC §119(e) for a provisional patent application, and incorporates by reference in its entirety all subject matter of the above-referenced application(s) to the extent such subject matter is not inconsistent herewith.

TECHNICAL FIELD

Systems and devices for delivering pre-determined quantities of an active ingredient, such as a therapeutic agent, are provided.

BACKGROUND

The ability to deliver an active ingredient, such as a therapeutic agent, locally to the site of need and over a prolonged period of time is important as a therapeutic method for many ailments and diseases. Many therapeutic agents are more effective if delivered at a specific site since they can be delivered in concentrated dosages at the point of interest, while maintaining an overall low dosage within the total body. Additionally, many therapeutic agents cannot be delivered by oral means because the molecules are too fragile to survive the digestive process, or because the molecules do not pass efficiently through the walls of the digestive organs. Some therapeutic agent therapies require long term dosing over the course of many months or years requiring frequent visits to a clinician for treatment. Furthermore, some therapeutic agents require delivery in places that are inconvenient for injection, such as in the eye or in internal organs. In all these cases, sustained therapeutic agent delivery through an implant or attached device would be of great benefit to patients undergoing treatment.

Accordingly, devices, systems and methods for producing desired time dosing profiles of therapeutic agents is desirable.

SUMMARY

The various embodiments and examples provided herein are generally directed to systems and methods for producing time-dependent release of a therapeutic agent. In some embodiments supporting structures containing chambers that hold an expandable material packaged with a therapeutic agent are provided. The chambers may be covered with a membrane that seals the material within the chamber. A second membrane composed of a porous material may be used to seal the second end of the chamber. This membrane may be of varying thickness, or may be partially covered with a non-porous material.

In one embodiment, a device for controlled release of an active ingredient is provided. The device includes a release aperture operably associated with a deflectable member, a base including a porous membrane layer, and at least one chamber juxtaposed between the release aperture and the porous membrane layer. The chamber contains a matrix that includes one or more active ingredients and an agent that expands when contacted with an aqueous solution. In general the device is suitable for implantation in a biological system.

In one aspect the deflectable member is a rupturable membrane. In other aspects the deflectable member is a deflectable cap comprised of a polymer, wax or gel. In yet another aspect the matrix includes a plurality of active ingredients. In this aspect, each active ingredient is released according to a specific release profile. Active ingredients include therapeutic agents such as pharmaceutical compounds. In another aspect the agent is a polymer, such as PLGA.

In some embodiments the base further includes a non-porous substrate layer associated with the porous membrane layer and including at least one channel suitable for contacting the porous membrane layer with an aqueous solution. The non-porous substrate layer may include a plurality of channels configured in a pre-determined pattern.

In other embodiments, the matrix includes hydrophilic binders, aqueous solution-soluble diluents, surfactants, lubricants, disintegrants, antioxidants, or non aqueous solution-soluble diluents, or any combination thereof.

In another embodiment, a device for controlled release of an active ingredient is provided. The device includes a release aperture operably associated with a deflectable member, a base including a porous membrane layer, and at least one chamber juxtaposed between the release aperture and the porous membrane layer. The chamber includes a first compartment including an active ingredient and a second compartment including an agent that expands when contacted with an aqueous solution. The device is suitable for implantation in a biological system.

In another embodiment, a system including a plurality of devices arrayed in a housing is provided. Each device in the system includes the same or different active ingredient. In addition, each device in the system includes the same or different release kinetics of the active ingredient.

In yet another embodiment, a device for controlled release of an active ingredient is provided. The device includes a plurality of chambers, each chamber including a release aperture operably associated with a deflectable member and an active ingredient. The device further includes a compartment including an agent that expands when contacted with an aqueous solution. The compartment is in expandable communication with each chamber of the device. The device also includes a base including a porous membrane layer adjacent to and in fluidic communication with the compartment. The device is suitable for implantation in a biological system.

In yet another embodiment, a computer-assisted method for designing and manufacturing a device or system for controlled release of an active ingredient in a biological system is provided. The method includes selecting at least one active ingredient for controlled release in a biological system, identifying a dosing profile suitable for eliciting an active ingredient-induced response in the biological system, and determining the geometries of the device or system suitable to obtain the desired dosing profile using finite element analysis. The device or system is manufactured according to the identified geometry. In some embodiments, the steps of identifying a dosing profile and determining the geometries of the device or system are repeated.

A device or system provided herein may be manufactured by any suitable technique, including lithography, micromachining, laser machining, precision machining or computer numerically controlled (CNC) machining, or any combination thereof.

In another embodiment, a device for controlled release of an active ingredient and suitable for implantation in a biological system is provided. The device includes a first non-porous plate, a second non-porous plate, and a matrix juxtaposed between the first and second plate. The matrix includes a first porous material including one or more active ingredients positioned in a pre-determined pattern, and a second porous material encapsulating the first porous material and in fluid communication with the biological system in which the device is implanted. In one aspect, the second porous material does not contain an active ingredient.

In another embodiment, a system that includes a plurality of devices is provided.

In yet another embodiment, a pulse therapy method for treating a subject is provided. The method includes identifying a subject having a condition and selecting one or more active ingredients suitable for treating the condition. The method further includes correlating the quantity and type of active ingredients with a pulse therapy dosing profile suitable for treating the condition. A device or system provided herein is suitably configured to deliver the active ingredient(s) according to the condition being treated and the dosing profile needed to treat the condition. In general the device or system is implanted in a subject in need of treatment.

The details of one or more embodiments of the disclosure are set forth in the accompanying drawings and the description below. Other features, objects, and advantages will be apparent from the description and drawings, and from the claims

BRIEF DESCRIPTION OF DRAWINGS

Like reference symbols in the various drawings indicate like elements.

DETAILED DESCRIPTION

Figure 1:
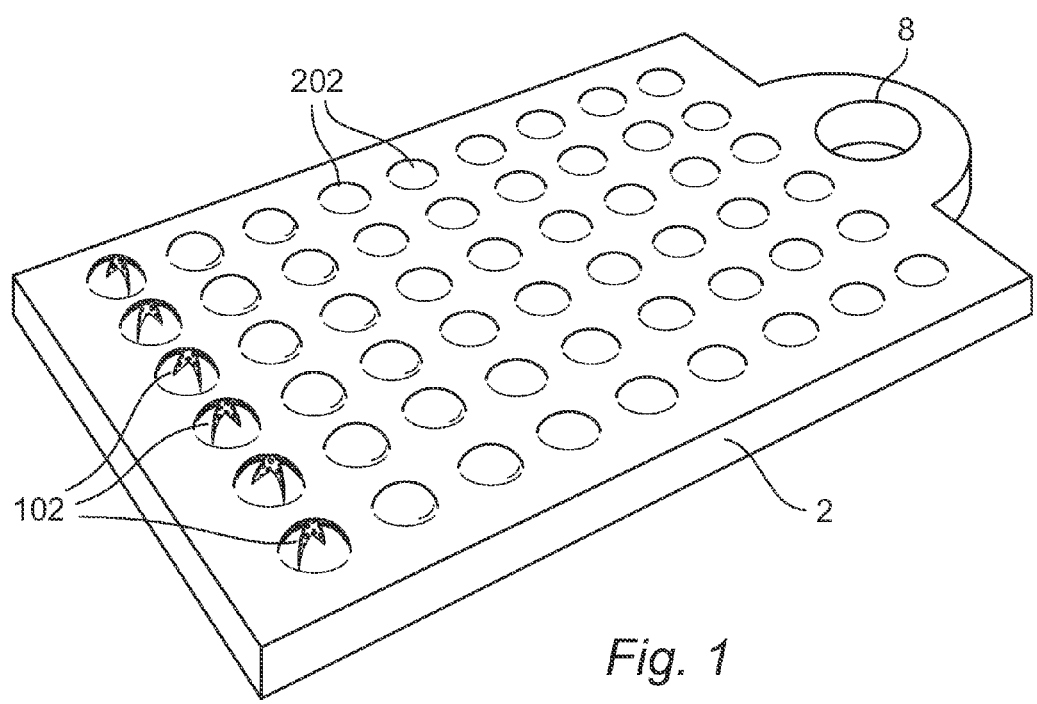
FIG. 1 depicts a perspective illustration of an exemplary embodiment of a device or system for delivering an active ingredient to a biological environment.

Each of the additional features and teachings disclosed below can be utilized separately or in conjunction with other features and teachings to provide a therapeutic agent delivery device for delivering time dependent dosing. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

The various embodiments provided herein are generally directed to systems and methods for producing a therapeutic agent delivery device that can deliver time dependent dosing without the need for electronics or power.

Accordingly, provided herein are devices, systems and methods designed to facilitate the controlled release of an active ingredient in a biological system. In general, the devices and systems include release aperture operably associated with a deflectable member, a base comprising a porous membrane layer, and at least one chamber containing a comprising an active ingredient and an agent that expands when contacted with an aqueous solution. The base may further include a non-porous substrate layer associated with the porous membrane layer and at least one channel suitable for contacting the porous membrane layer with an aqueous solution. In general the deflectable member can be a rupturable membrane or a deflectable cap comprises of a polymer, wax or gel.

Devices and systems provided herein can be used to deliver active ingredients to a biological environment to effect changes in that environment. Accordingly, in one aspect an active ingredient is a therapeutic agent. In some applications a device or system containing a therapeutic agent can be implanted in an ocular environment to treat age related macular degeneration (AMD). Age related macular degeneration is the leading cause of blindness in people over age 65. The National Eye Institute estimates that there are 1.6 million individuals with AMD in the United States alone. Macular degeneration is the physical disturbance of the center of the retina called the macula, the part of the retina which is capable of our most acute and detailed vision. Currently, there is no known cure for AMD. However, new therapies are being developed which show promise in controlling the progression of the disease. Some of these treatments include frequent administration of protein-based therapeutic agent formulations such as Lucentis (ranibizumab) and Avastin (bevacizumab) directly into the eye. Since these therapeutic agents consist of large protein molecules which cannot be administered through oral formulations, patients suffering from AMD have to receive injections directly into their eyes once every month. The highly invasive nature of the treatment and limitations in controlling an effective therapeutic agent concentration in the eye over a prolonged period of time still leave these delivery methods far from ideal. Small, programmable therapeutic agent delivery implants would be a highly valuable alternative.

In some aspects, the active ingredient is a therapeutic agent, such as pharmaceutical compound. The compound can be included in a suitable matrix or carrier. The matrix or carrier can further include hydrophilic binders, aqueous solution-soluble diluents, surfactants, lubricants, disintegrants, antioxidants, or non aqueous solution-soluble diluents, or any combination thereof.

The term "active ingredient" is intended to mean any compound having a therapeutic effect, and which is suitable for administration in a device provided herein. Active ingredients include non-peptide organic molecules, small peptides and peptide mimetics, and the like, as well as their pharmaceutically acceptable salts. The active ingredient itself may be stable upon storage or under stress conditions, but when formulated with one or more carriers it shows stability issues.

The term "carrier" is intended to mean such carriers which are commonly used in the pharmaceutical chemistry for preparing pharmaceutical formulations, see e.g., Remington: The Science and Practice of Pharmacy, 19th Edition (1995); "Therapeutic agents and the pharmaceutical sciences", vol. 81, 1997. In particular such one or more carriers are selected from, but not limited to, hydrophilic binders, aqueous solution-soluble diluents, surfactants, lubricants, disintegrants, antioxidants, non aqueous solution-soluble diluents and/or other fillers known to the skilled person.

The term "pharmaceutically acceptable salt" represents salt forms of an active ingredient, e.g. a compound of formula I, that are physiologically suitable for pharmaceutical use. The pharmaceutically acceptable salts can exist in conjunction with an active ingredient as acid addition primary, secondary, tertiary, or quaternary ammonium, alkali metal, or alkaline earth metal salts. Within the present invention, the active ingredient may be prepared in the form of a salt such as pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, maleic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The term "hydrophilic binder" represents binders commonly used in the formulation of pharmaceuticals, such as polyvinylpyrrolidone, copolyvidone (cross-linked polyvinylpyrrolidone), polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "aqueous solution-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "non aqueous solution-soluble diluent" represents compounds typically used in the formulation of pharmaceuticals, such as calcium phosphate, calcium sulfate, starches, modified starches and microcrystalline cellulose.

The term "non aqueous solution-soluble diluent with non-swelling properties" represents the non aqueous solution-soluble diluents as indicated above, but excluding starches and modified starches and the like.

The term "surfactant", as used herein, represents ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, alcohols and phospholipids.

The term "antioxidant" represents the three groups of antioxidants, true antioxidants, reducing agents and antioxidant synergists, such as tocopherols, tocopherolesters, alkyl gallates, butylated hydroxyanisole, butylated hydroxytoluene, ascorbic acid, citric acid, edetic acid and its salts, lecithin and tartaric acid.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably, the disintegrant is a modified cellulose gum such as e.g. cross-linked sodium carboxymethylcellulose.

The term "active ingredient" includes therapeutic agents (i.e., pharmaceutical compounds) which are suitable for inclusion in a device or system provided herein. Such compounds include, but are not limited to, anti-angiogenic compounds such as bevacizumab, ranibizumab, pegaptanib, and other compounds in the angiogenic cascade. Also included are glucocorticosteroids such as dexamethasone, triamcinolone acetonide, fluocinolone acetonide and other comparable compounds in the corticosteroid and cortisene families. Also included are compounds such as antacids, anti-inflammatory substances, coronary dilators, cerebral dilators, peripheral vasodilators, anti-infectives, psychotropics, anti-manics, stimulants, anti-histamines, laxatives, decongestants, vitamins, gastrointestinal sedatives, anti-diarrheal preparations, anti-anginal therapeutic agents, vasodilators, anti-arrhythmics, anti-hypertensive therapeutic agents, vasoconstrictors and migraine treatments, anti-coagulants and anti-thrombotic therapeutic agents, analgesics, anti-pyretics, hypnotics, sedatives, anti-emetics, anti-nauseants, anticonvulsants, neuromuscular therapeutic agents, hyper- and hypoglycemic agents, thyroid and anti-thyroid preparations, diuretics, antispasmodics, uterine relaxants, mineral and nutritional additives, anti-obesity therapeutic agents, anabolic therapeutic agents, erythropoietic therapeutic agents, anti-asthmatics, bronchodilators, expectorants, cough suppressants, mucolytics, therapeutic agents affecting calcification and bone turnover and anti-uricemic therapeutic agents. Specific therapeutic agents include gastro-intestinal sedatives such as metoclopramide and propantheline bromide; antacids such as aluminum trisilicate, aluminum hydroxide, ranitidine and cimetidine; anti-inflammatory therapeutic agents such as phenylbutazone, indomethacin, naproxen, ibuprofen, flurbiprofen, diclofenac, dexamethasone, prednisone and prednisolone; coronary vasodilator therapeutic agents such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic therapeutic agents such as flurazepam, diazepam, temazepam, amitryptyline, doxepin, lithium carbonate, lithium sulfate, chlorpromazine, thioridazine, trifluoperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistaminc therapeutic agents such as diphenhydramine, diphenylpyraline, chlorpheniramine and brompheniramine; anti-diarrheal therapeutic agents such as bisacodyl and magnesium hydroxide; the laxative therapeutic agent, dioctyl sodium sulfosuccinate; nutritional supplements such as ascorbic acid, alpha tocopherol, thiamine and pyridoxine; anti-spasmodic therapeutic agents such as dicyclomine and diphenoxylate; therapeutic agents affecting the rhythm of the heart such as verapamil, nifedipine, diltiazem, procainamide, diisopyramide, bretylium tosylate, quinidine sulfate and quinidine gluconate; therapeutic agents used in the treatment of hypertension such as propranolol hydrochloride, guanethidine monosulphate, methyldopa, oxprenolol hydrochloride, captopril and hydralazine; therapeutic agents used in the treatment of migraine such as ergotamine; therapeutic agents affecting coagulability of blood such as epsilon aminocaproic acid and protamine sulfate; analgesic therapeutic agents such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic therapeutic agents such as phenyloin sodium and sodium valproate; neuromuscular therapeutic agents such as dantrolene sodium; substances used in the treatment of diabetes such as tolbutamide, disbenase glucagon and insulin; therapeutic agents used in the treatment of thyroid gland dysfunction such as triiodothyronine, thyroxine and propylthiouracil, diuretic therapeutic agents such as furosemide, chlorthalidone, hydrochlorothiazide, spironolactone and triamterene; the uterine relaxant therapeutic agent ritodrine; appetite suppressants such as fenfluramine hydrochloride, phentermine and diethylproprion hydrochloride; anti-asthmatic and bronchodilator therapeutic agents such as aminophylline, theophylline, salbutamol, orciprenaline sulphate and terbutaline sulphate; expectorant therapeutic agents such as guaiphenesin; cough suppressants such as dextromethorphan and noscapine; mucolytic therapeutic agents such as carbocisteine anti-septics such as cetylpyridinium chloride, tyrothricin an chlorhexidine; decongestant therapeutic agents such as phenylpropanolamine and pseudoephedrine; hypnotic therapeutic agents such as dichloralphenazone and nitrazepam; anti-nauseant therapeutic agents such as promethazine theoclate; haemopoietic therapeutic agents such as ferrous sulphate, folic acid and calcium gluconate; uricosuric therapeutic agents such as sulphinpyrazone, allopurinol and probenecid; and calcification affecting agents such as biphosphonates, e.g., etidronate, pamidronate, alendronate, residronate, teludronate, clodronate and alondronate.

In one embodiment, a device that includes a base composed of regions containing chambers is provided. Each chamber may contain a material that expands in the presence of an aqueous solution. Each chamber may also contain an active ingredient, such as a therapeutic agent, which is desired to be released at a predetermined time. Covering each chamber is a deflectable material designed to be displaced when expandable material in the chamber increases in volume. Once the deflectable material is displaced the aperture of the chamber is opened to the environment. Also covering each chamber is second thin membrane be associated with a porous membrane and/or non-porous substrate layer. These features may facilitate contacting of an aqueous solution with the content of a chamber at a controlled rate. The expansion rate of an expandable material contained in the chamber may determine when the deflectable member is deflected or displaced. Upon deflection or displacement, the content of a chamber comes in contact with the environment in which the device or system has been placed.

The porous membrane's diffusion rate may be controlled by the amount of non-porous material covering the membrane. Alternatively, the porous material may be embossed to produce regions of different thickness, effectively controlling the diffusion rate through the membrane by thickness. Each chamber is covered by a porous membrane with a different seep or diffusion rate, as determined by the non-porous covering or by the variations in thickness created during manufacture of the membranes. The seep or diffusion rate controls the rate of swelling in the expandable material. Chambers that are covered by porous membranes with high diffusion rates will have swelling rates that are high. Chambers that are covered by porous membranes with low diffusion rates will have swelling rates that are slow.

Expandable materials will rupture their membranes allowing aqueous solution to flow into the chamber and release the therapeutic agent from within the polymer. Materials in chambers containing fast seeping or diffusing membranes will swell faster and therefore rupture their membranes sooner than those in chambers with slow diffusing membranes. In this manner, the specific manner in which the diffusing membranes are prepared will program the ultimate time profile of the therapeutic agent dosing.

Variations on this principle are also described whereby the deflectable member may be designed to deflect or displace at different times, even if the volumetric expansion of the chamber material is constant. Examples of this include adjusting the structure of the deflectable member, or adding strengthening materials to the deflectable member. Other variations include utilizing a deflectable member that resembles a plug or cap. Such structures are more likely to be displaced from the aperture of a chamber as opposed to rupturing.

Alternative design methods include using micromachining to place two or more different materials adjacent to each other. At least one of the materials may contain a therapeutic agent or chemical of interest. By controlling the geometry where the first material and second material are in a device or system, one can control when therapeutic agent or chemical is released from the system.

Also provided herein are computer simulations to design the therapeutic agent delivery device. The device is designed to be most readily manufactured by computer controlled process. In particular, one embodiment uses a 2-D sandwich composite of at least two materials to produce a desired delivery profile. The 2-D nature of the device makes it easy to fabricate using computer generated molds, dies, or cutting shapes.

Referring to FIG. 1, an exemplary device for delivering an active ingredient to a biological system is depicted. The device includes base 2 containing one or more chambers 102 fabricated within it. Base 2 is generally comprised of material(s) refractory to the diffusion of aqueous solutions. Base 2 functions to inhibit or prevent the unintended exposure of chamber contents to an aqueous solution from the external environment. Each chamber includes a release aperture operably associated with a deflectable member 202 designed to deflect or dislocate in the event that the material within it expands. In some aspects the deflectable member ruptures to expose the contents of the chamber to the outside environment. Exemplary rupturable material includes membrane and membrane-like material. In other aspects the deflectable member hingably opens to expose the contents of the chamber to the outside environment. In yet another aspect the deflectable member is partially or completely displaced from the aperture of the chamber. During use the expandable material within the chamber expands beyond a critical volume. The expansion forces the deflectable member to deflect or dislocate creating an opening to the chamber. The contents of the chamber are exposed to the environment in which the device or system resides. The housing may contain external elements 8 that facilitate the deployment of the device into, for example, a biological environment.

Figure 2:
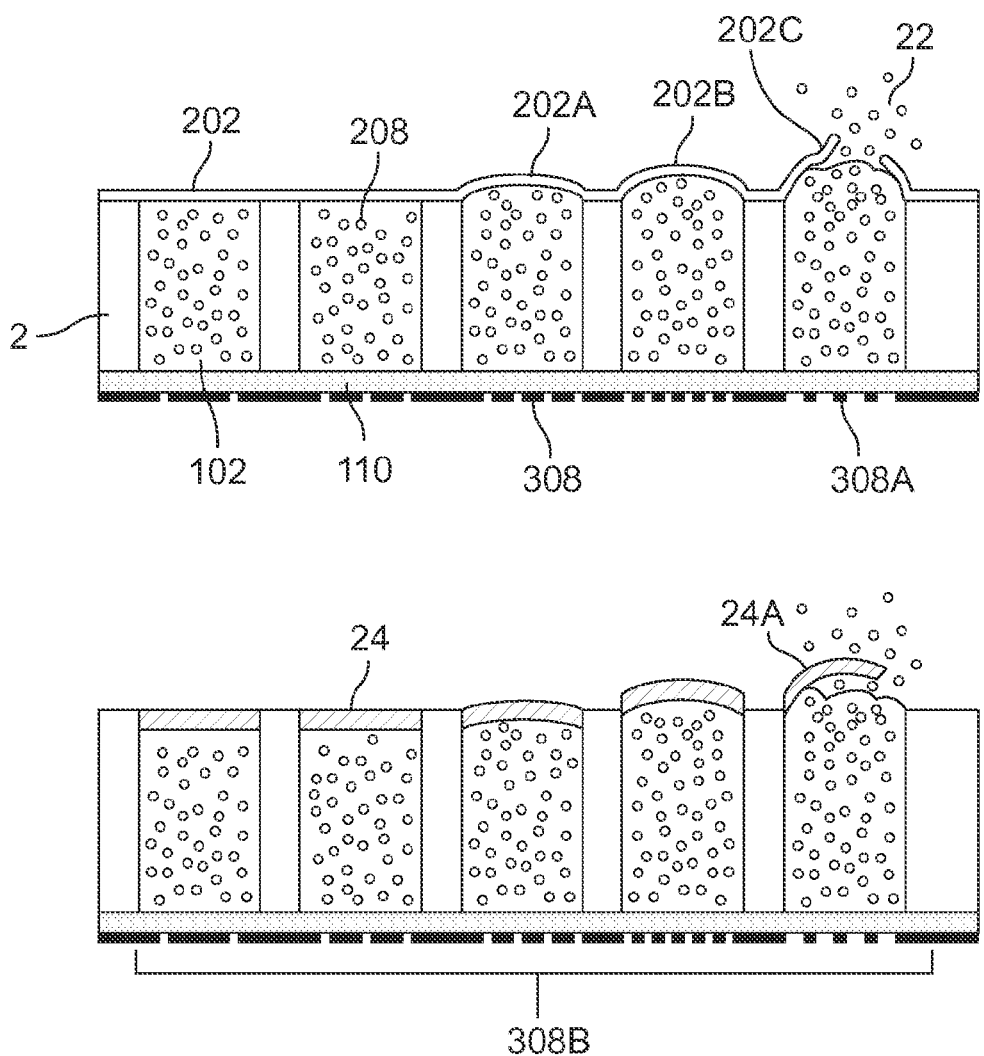
FIG. 2 depicts a cross-sectional view of an exemplary embodiment of a device or system for delivering an active ingredient to a biological environment.

Referring to FIG. 2, the device base 2 contains chambers 102 which act as reservoirs for a therapeutic agent of interest and an expandable material. In one embodiment, the therapeutic agent and the expandable material are combined together to form a single compound 208. The expandable material may be any composition suitable for combining with an active ingredient. In some aspects the expandable material may be a polymer. The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. Examples of polymers include but are not limited to, poly-alpha-hydroxy acid esters such as, polylactic acid (PLLA or DLPLA), polyglycolic acid, polylactic-co-glycolic acid (PLGA) polylactic acid-co-caprolactone; polyethylene glycol and polyethylene oxide; polyvinyl pyrrolidone; polyorthoesters; polysaccharides and polysaccharide derivatives such as polyhyaluronic acid, poly (glucose), polyalginic acid, chitin chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

In some aspects the expandable material is PLGA, a bulk eroding biodegradable polymer. Biodegradable polymers that expand and hydrolytically degrade include PLGA composite polymers which composed of PLA and PGA. Depending on the ratio of PLA and PGA and molecular weight, the polymer can breakdown at different rates in the presence of aqueous solution. Additional polymers include poly[(ethyl glycinate)(benzyl amino acetohydroxamate) phosphazene] (PEBP), a biodegradable polymer which may be used to encapsulate a therapeutic agent of interest. Other polymers include anhydride polymers, such as poly(sebacic anhydride)-3-poly(ethylene glycol) (PSP) or poly(sebacic anhydride-co-trimellitylimidoglycine)-β-poly(ethylene glycol) (PSTP).

In another embodiment, a third material such as an inert fluid is used to fill the remaining space of the chamber, ensuring no trapped air remains in the chamber. At a first position of a chamber a deflectable member 202 holds the expandable material and therapeutic agent within the chamber. At a second position the chamber is in contact with a porous membrane layer 110 associated with the base. The chamber is generally juxtaposed between the release aperture and the porous membrane layer. The porous membrane layer 110 generally allows an aqueous solution to seep through into the chamber. The porous membrane layer 110 may be associated with a patterned non-porous material forming a non-porous substrate layer 308 that limits the exposure of defined regions of the porous material forming the porous membrane layer 110 to the aqueous environment. The material within the chamber swells in response to the aqueous solution seeping or diffusing into the chamber, resulting in the deflection of the deflectable member to become an expanded deflectable member 202A. The thickness and porosity of the porous membrane layer 110, combined with the amount of openings in the patterned non-porous coating of the non-porous substrate layer 308, determines the rate that aqueous solution seeps or diffuses into the chamber. Chambers that have less non-porous coating in the non-porous substrate layer 308 blocking the membrane will experience faster material swelling, thus causing the deflectable member to become a bulging deflectable member 202B. The chambers that are covered by the least non-porous coating covering the a porous membrane, such as non-porous substrate layer 308A, will have the fastest seep or diffusion rate, and will cause their deflectable members to more quickly become a broken deflectable member 202C. Different non-porous coating sizes can may be used to form a plurality of variable non-porous substrate layer 380B sizes, with different size impacting time release of therapeutic agents from these chambers into the surrounding fluid 22.

In another embodiment, the deflectable member is configured as a plug or cap. Referring to FIG. 2, a polymer, wax, gel or similar material may form the plug or cap 24 that is the deflectable member. Plugs or caps can be manufactured by any method. For example, photolithography may be used to define a photosensitive polymer, forming plugs or caps at each chamber. The plugs or caps are pushed up when the swelling material expands. In this event the plug is removed and results in a dislodged cap 24A, releasing the therapeutic agent from the reservoir.

Figure 3:
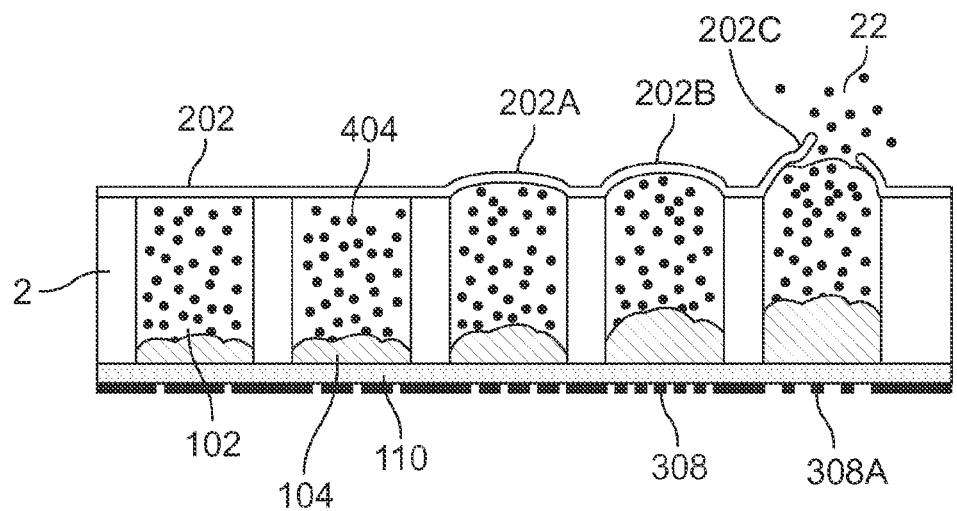
FIG. 3 depicts a cross-sectional view of an exemplary embodiment of a device or system for delivering an active ingredient to a biological environment.

Referring to FIG. 3, the device base 2 contains chambers 102 which act as reservoirs for a therapeutic agent 404 of interest and a separate expandable material 104. In this embodiment, the therapeutic agent 404 and the expandable material 104 are separate (e.g., not mixed or comprising a mixture) to form two distinct compounds. In a first position the chamber may be sealed by a deflectable member 202 that contains the polymer 104 and therapeutic agent 404 within the chamber. At a second position the chamber is in contact with a porous membrane layer 110 associated with a patterned non-porous substrate layer 308. The porous membrane allows an aqueous solution to seep through into the chamber. The patterned non-porous substrate layer 308 limits the regions of porous material exposed to the aqueous solution. The material within the chamber expands in response to the aqueous solution seeping or diffusing into the chamber, causing the sealed membrane to deflect and become an expanded deflectable member 202A. The thickness and porosity of the porous membrane layer 110, combined with the number of openings in the patterned non-porous substrate layer 308, determine the rate that aqueous solution seeps or diffuses into the chamber. Chambers that have less non-porous coating in the non-porous substrate layer 308A blocking the porous membrane will experience increased expandable material expansion, thus causing the deflectable member to expand more quickly first becoming an expanded deflectable member 202A, then a bulging deflectable member 202B, and eventually, a broken deflectable member 202C.

In other aspects, different quantities of expandable material may be included in the chambers depicted in FIG. 3. The expansion rate of many expandable polymers may be dependent on the total volume of the polymer in the chamber. Thus, chambers containing more expandable material may expand and deflect or dislocate the associated deflectable member more quickly than those chambers containing less expandable material.

Figure 4:
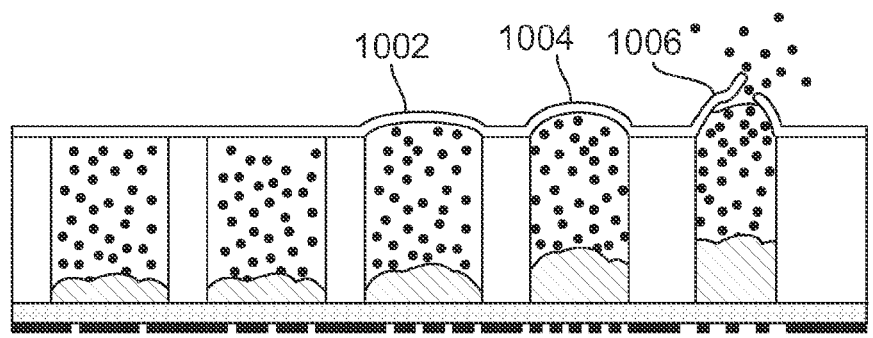
FIG. 4 depicts a cross-sectional view of an exemplary embodiment of a device or system for delivering an active ingredient to a biological environment.

Referring to FIG. 4, the configuration of the base and associated chambers may be used to control the deflection or displacement rate of the deflectable member. In this example, the surface area of the membrane may be determined by the structure of the base or associated chamber(s) 1002, 1004, 1006. For the same amount of volumetric increase within a chamber, apertures with smaller surface areas will result in deflectable members that displace or deflect more than apertures with larger surface areas. This is caused by the hydraulic principle which states that volumetric flow should be constant throughout the chamber. Thus, a smaller deflectable member 1006 will, for example, rupture earlier than a medium deflectable member 1004. A medium deflectable member 1004 will rupture earlier than a larger deflectable member 1002. This feature is readily exploited in an embodiment that modifies the deflectable member area associated with a chamber.

Additionally, deflectable members may include additional features and materials associated with them in order to modify their physical properties and therefore their displacement or deflection properties. These optional features and materials may be used to preprogram their time of displacement or deflection.

Figure 5:
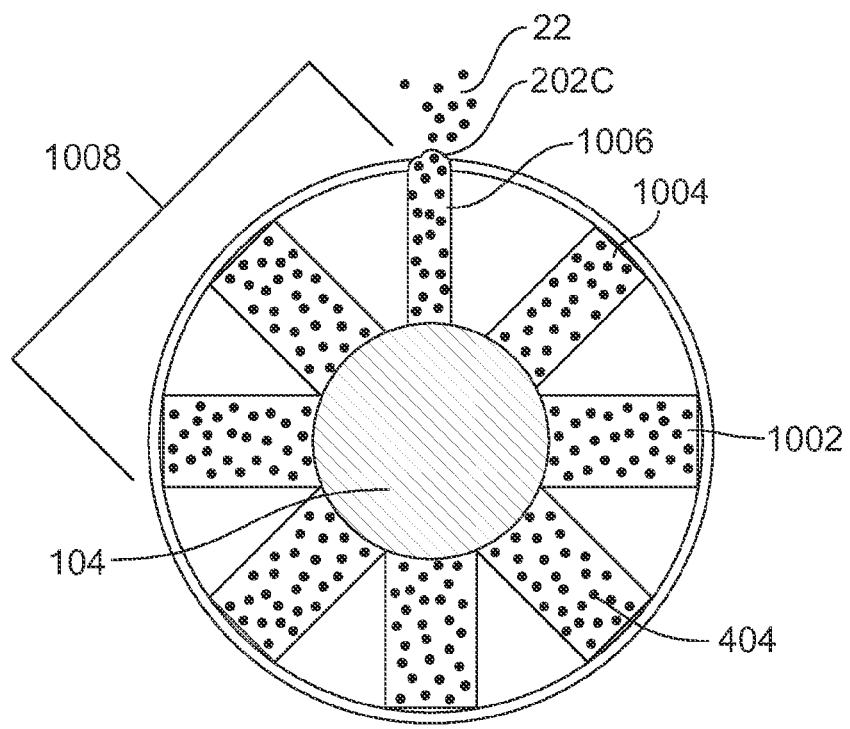
FIG. 5 depicts an over-head view of an exemplary embodiment of a device or system for delivering an active ingredient to a biological environment. The chambers are depicted in a circular configuration.

It is understood that that the chambers of a device or system can be arranged in any configuration suitable for delivery of an active ingredient to a biological environment. FIG. 5 provides additional exemplary configurations of a device or system provided herein. The plurality of chambers 1008 shown in FIG. 5 are arranged in a circular configuration. In one example the deflectable members may be constructed to delineate the time of opening (see e.g., FIG. 4). Accordingly, the chambers may share a common expanding material 104. As the expanding material increases its volume, it pushes against all deflectable members equally. Those deflectable members designed to burst early will release their therapeutic agent first.

Figure 6:
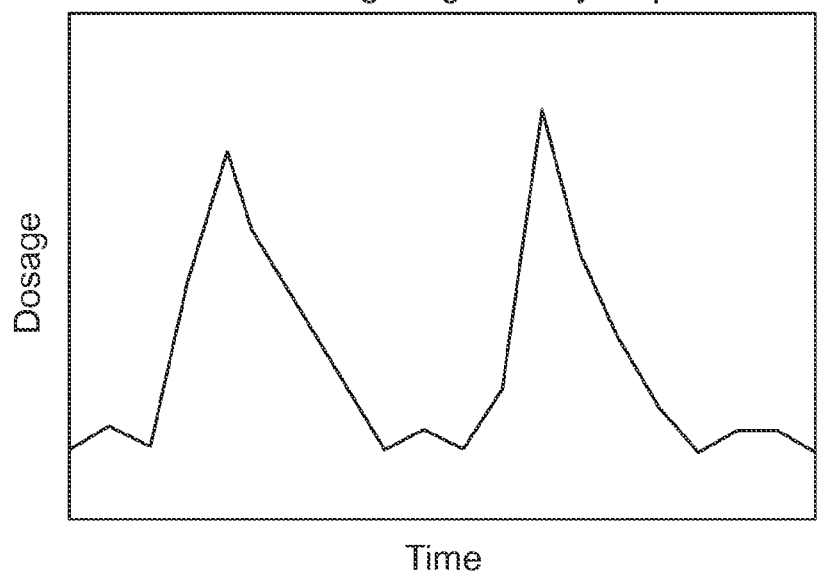
FIG. 6 depicts a graph showing an exemplary release profile of an active ingredient from a device or system provided herein.

Referring to FIG. 6, a dosage profile over time may be controlled by adjusting the seep rate into each chamber, which in turn may be controlled by the non-porous layer associated with the porous membrane at each chamber. The dosage may be pulsatile. For example, the first dose delivered when a first chamber associated with a smaller deflectable member 1006 is deflected or displaced. The second dose may be delivered when a medium deflectable member 1004 or larger deflectable member 1002 associated with an aperture of the second chamber is deflected or displaced. Accordingly, the present devices, systems and methods encompass the pulsatile delivery of active ingredients, such as pharmaceutical compounds. By "pulsatile" is meant that a plurality of therapeutic agent doses are released at spaced apart intervals of time. Accordingly, the devices and systems may be designed, configured and manufactured to possess release profiles (e.g., release kinetics) suitable for treating specific conditions or multiple conditions. It is understood that such devices and systems can include a plurality of active ingredients each possessing a specific release profile suitable for treating multiple conditions. A pulsatile delivery system is capable of providing, for example, one or more immediate release pulses at predetermined time points after a controlled lag time or at specific sites. The system or device allows for pulsatile therapeutic agent delivery, and the administration of differing sized dosages of active ingredients at different times automatically, pursuant to a pre-programmed dosage profile utilized to design, configure and manufacture a device or system provided herein. Exemplary release profiles include those that correspond to desired peaks and troughs related to disease symptoms.

Figure 7:
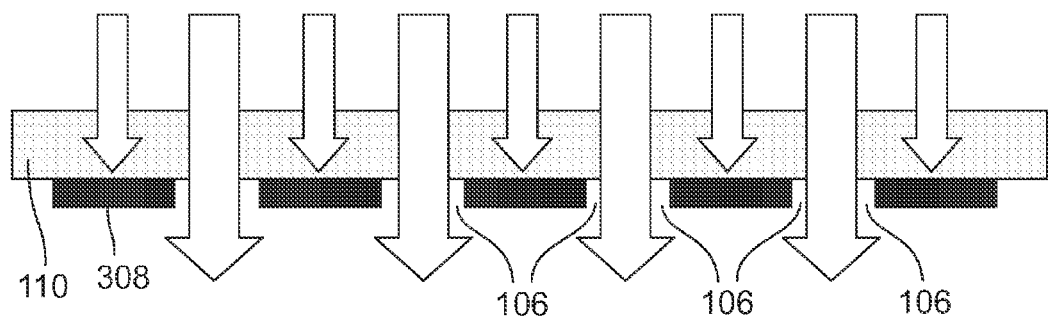
FIG. 7 is a cross-sectional view of a diffusing membrane showing how a patterned, external coating can control the diffusion rate through the membrane in the presence of a non-porous substrate layer.

Referring to FIG. 7 a porous membrane layer 110 that allows the passage of an aqueous solution (or other chemicals) is depicted. A patterned non-porous material forms a non-porous substrate layer 308 covering part of the porous membrane layer 110. Since an aqueous solution and chemicals cannot pass through certain regions of the non-porous substrate layer 308, the non-porous substrate layer 308 may include a plurality of channels 106 configured in a pre-determined pattern. Diffusion of aqueous solution or chemicals occurs primarily through this plurality of channels 106. Therefore, the volumetric rate of diffusion can be controlled by the pattern of a plurality of channels 106 associated with this non-porous substrate layer 308.

Figure 8:
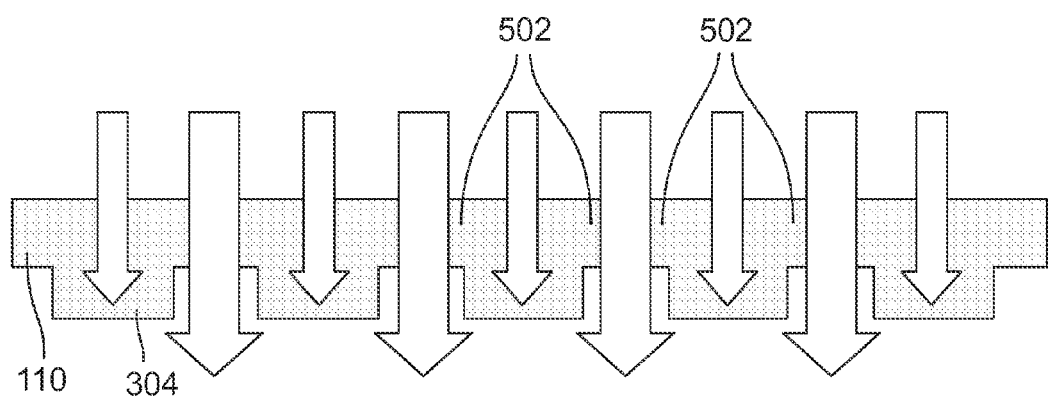
FIG. 8 depicts a cross-sectional view of an exemplary embodiment of a device or system for delivering an active ingredient to a biological environment in the absence of a non-porous substrate layer.

In other embodiments, a non-porous substrate layer is not needed to control diffusion. Instead, the rate of diffusion may be modulated by controlling the thickness of the porous membrane at various locations. Referring to FIG. 8, a porous membrane layer 110 may be shaped to have regions of different thicknesses. Since a diffusion rate through thick regions 304 is slower than through thin regions 502, the diffusion of aqueous solution or chemicals occurs primarily through the thin regions 502. Therefore, the volumetric rate of diffusion can be controlled by the patterned thickness of the porous membrane.

Figure 9:
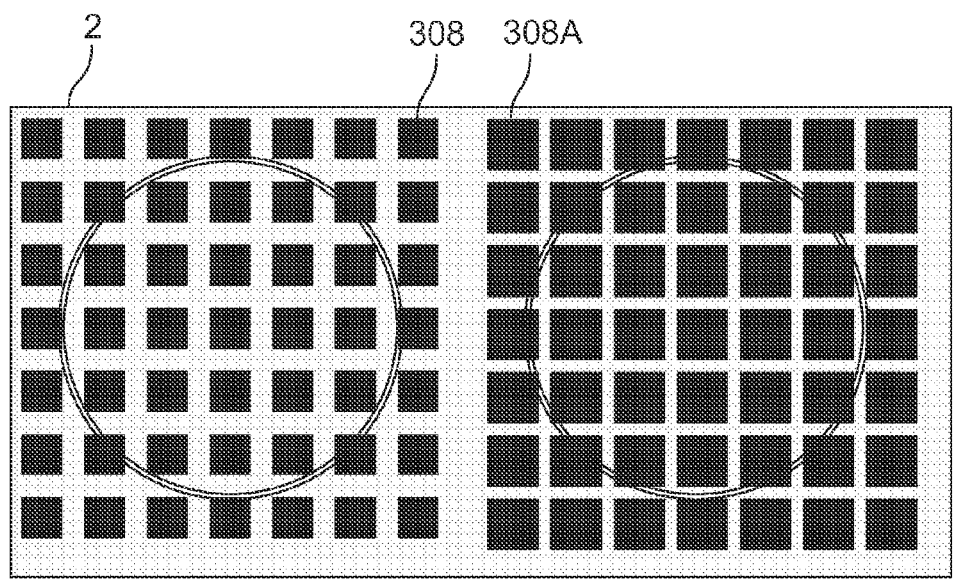
FIG. 9 depicts a plane view of an exemplary embodiment of a device or system for delivering an active ingredient to a biological environment. Exemplary configurations of patterned non-porous substrate layer are depicted.

In other embodiments, a single device or system may include multiple chambers having porous membranes of varying porosity and/or non-porous substrate layers of varying channel patterns. For example, and referring to FIG. 9, two chambers with are depicted side by side in the base 2 of a single device. The diffusion rate of aqueous solution or chemicals across a first porous membrane in a first chamber and a second porous membrane associated with a second chamber would be the same since they share the same membrane material. However, since the porous membrane associated with the first chamber is covered with a pattern of non-porous substrate layer 308A, the diffusion rate is reduced to be proportional to the channels that are not covered by the material. A porous membrane associated with a second chamber is covered with a different pattern of non-porous substrate layer 308, resulting in a different diffusion rate, in this example, lower diffusion. The two chambers which are identical in every other way have different diffusion rates, each of which is controlled by the patterning of the material on the surface. The non-porous material may be a photosensitive polymer and the patterning can be performed by standard lithographic methods.

Figure 10:
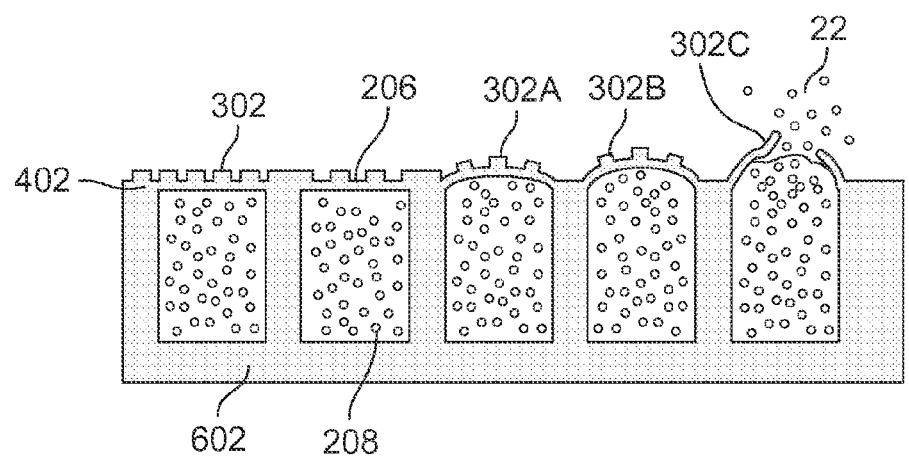
FIG. 10 depicts a cross-sectional view of an exemplary embodiment of a device or system for delivering an active ingredient to a biological environment.

In another embodiment, a deflectable member 302 may be comprised of porous material 402 and patterned to accommodate different rates of diffusion through different regions of the deflectable member. For example, and referring to FIG. 10, a cross section of a device made from a single material is provided. In this device the bulk material 602 is also used as the porous membrane material. Since the bulk material 602 is much thicker than the membrane material, aqueous solution diffusion occurs primarily through the porous membranes. The bulk encapsulates chambers containing expandable material and therapeutic agent forming a single compound 208. The deflectable member 302 is aqueous solution permeable and contains channels 206 that control the diffusion rate of aqueous solution into the chambers. Different structure patterns associated with the deflectable member result in different diffusion rates, and thus different rates of polymer swelling. In this embodiment, the diffusion membrane and the rupturing membrane are the same membrane. Ultimately, the swelling polymer expands sufficiently to form an expanded deflected member 302A, later a bulging deflecting member 302B, leading to bursting of the thin membrane, resulting in a broken deflected member 302C, thereby causing release of the therapeutic agent into the surrounding fluid 22.

Figure 11:
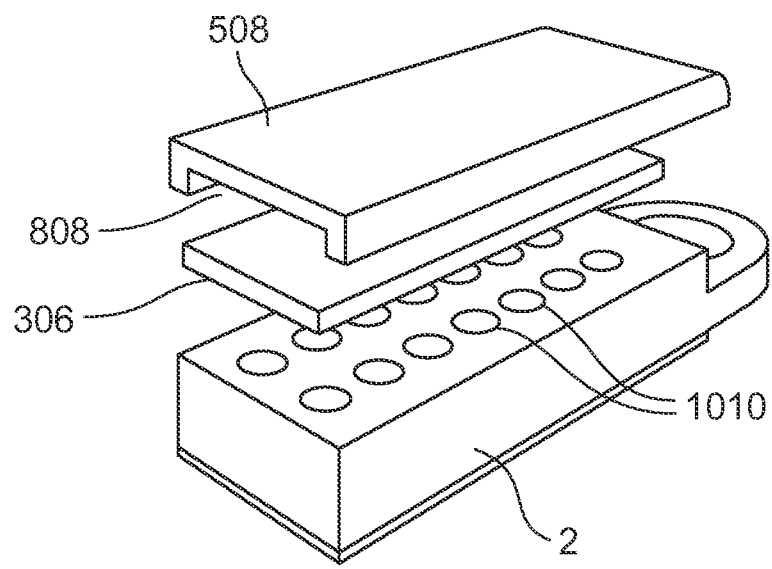
FIG. 11 depicts an exemplary embodiment of a device or system for delivering an active ingredient to a biological environment. The exemplary illustration includes a non-porous casing associated with the base of a device or system.

In other embodiments, a device or system is comprised of a base that is semi-permeable or non-permeable to aqueous solutions. As illustrated in FIG. 11, a non-permeable base 2 may be manufactured with a plurality of chambers 1010 containing an active ingredient to be delivered to a biological environment. The chambers may be covered by a layer of degradable material 306 that is placed over substantially all of the base. Surrounding the degradable material may be a non-permeable casing 508 with an opening 808 that provides a path for the fluid to dissolve the degradable material 306. As the degradable material 306 is removed, the active ingredient-filled chambers are exposed to the aqueous solution initiating the release of the contents into the surrounding environment. The base and casing may also be constructed of a fluid degradable material.

Figure 12:
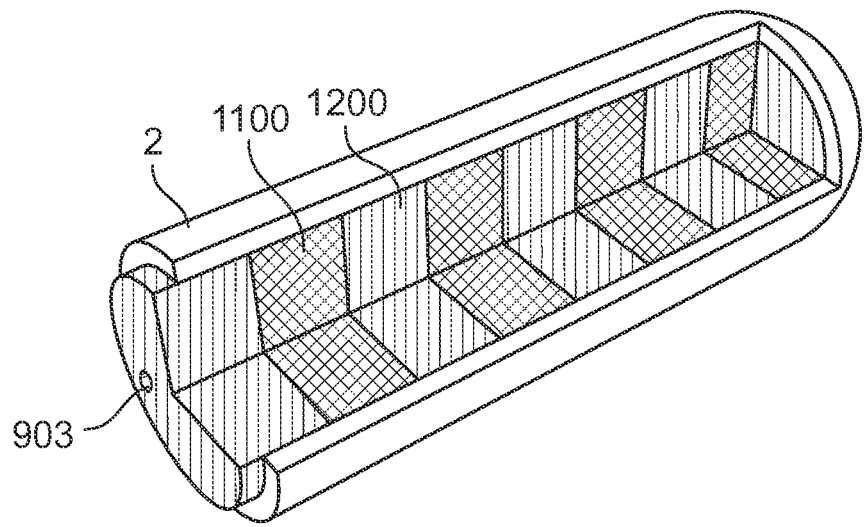
FIG. 12 depicts an exemplary embodiment of a device or system for delivering an active ingredient to a biological environment. The exemplary illustration shows a device having multiple materials functionally encapsulated in a cylindrical configuration which facilitates the degradation of the materials in a pre-determined sequence.

In another embodiment, biodegradable materials may be micropatterned as depicted in FIG. 12. In this embodiment, a device includes a base 2 which is not highly permeable to aqueous solution. The base may be made from a degrading polymer if desired. In some embodiments, the base should not degrade during the period that therapeutic agent is to be administered to the patient. In other embodiments, the housing may degrade during the period of delivery. The housing has one or more openings 908 that allow fluid to come into contact with a degradable or diffusing material. This material may be filled with any active ingredient, including a therapeutic agent. In some aspects, between doped materials 1100 that contain a therapeutic agent there may be undoped materials 1200 that contain no therapeutic agent. As fluid contacts material from the opening, it slowly removes material from that opening, allowing the fluid to penetrate deeper into the base. Since therapeutic agent loaded doped materials 1100 are alternated between non-loaded undoped materials 1200, the therapeutic agent dosing is pulsed over time. The layering may include several different therapeutic agents to produce complex pulsatile therapeutic agent delivery profiles. In this embodiment, the device may contain materials that are bulk eroding, surface eroding, or both.

Figure 13:
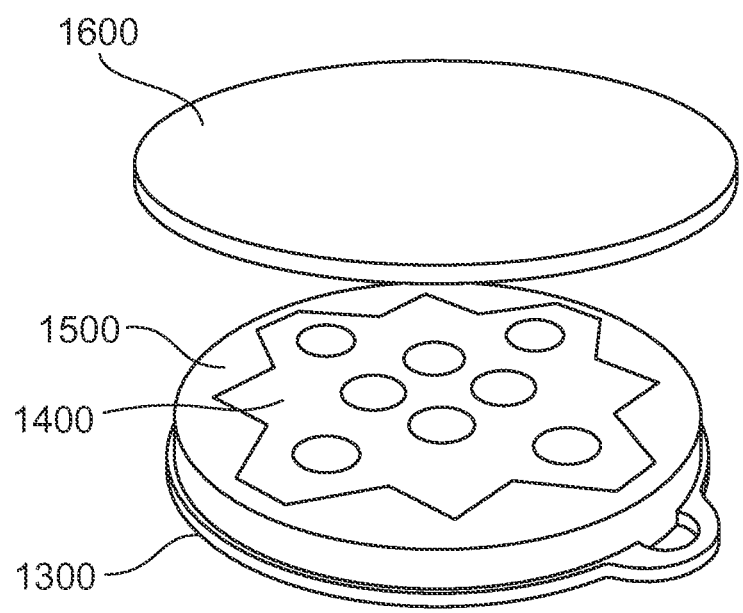
FIG. 13 depicts an exemplary embodiment of a device or system for delivering an active ingredient to a biological environment. The exemplary illustration shows a device that includes at least two materials and has a 2-D layered structure.

In another embodiment, a pattern of therapeutic agent filled material may be encapsulated within another non-therapeutic agent filled material. Referring to FIG. 13, a plate of non-porous material 1300 may be used to hold a flat patterned layer of therapeutic agent filled material 1400. The therapeutic agent filled material, such as a polymer, may be shaped with various openings and hollow sections. Surrounding and encapsulating the therapeutic agent filled material may be a non-therapeutic agent filled material 1500. The composite of therapeutic agent filled material 1400 and non-therapeutic agent filled material 1500 may be capped by a second flat non-porous plate 1600. Since the device may be capped by non-porous material at the top and bottom, fluid can contact the therapeutic agent-filled and filler materials from alternative regions. In this manner, the release rate of therapeutic agent may be controlled. As the fluid dissolves the materials it seeps deeper into the device and contacts varying amounts of therapeutic agent filled material. The amount of therapeutic agent that comes in contact with the fluid depends on the shape of the therapeutic agent-filled region, which is controlled during manufacture.

Figure 14:
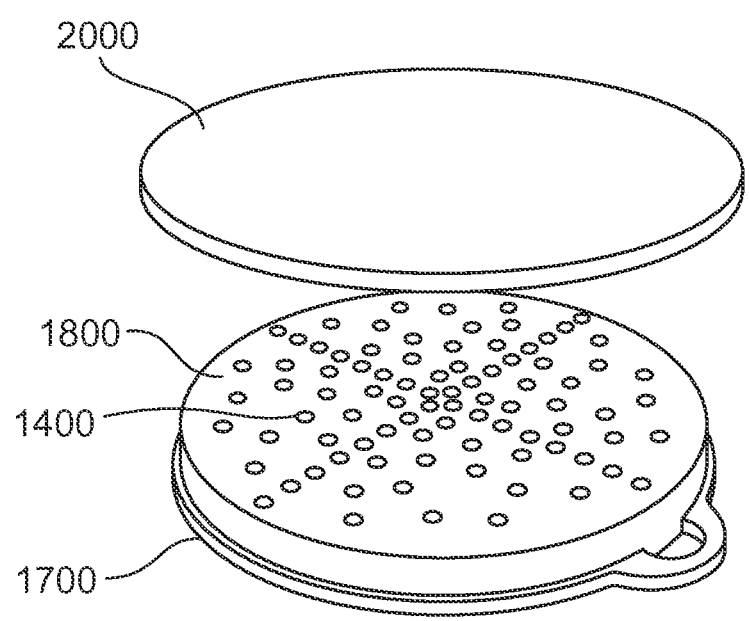
FIG. 14 depicts an exemplary embodiment of a device or system for delivering an active ingredient to a biological environment.

In other embodiments, and as depicted in FIG. 14, a non-porous disk 1700 may be laminated with an inert, degradable material, such as a polymer. Embedded within the inert material 1800 at predetermined regions are therapeutic agent filled materials 1400. Substantially all of the device may be capped with a second non-porous disk 2000. The resulting device resembles a sandwich structure that allows fluid to degrade the structure from the sides only, releasing therapeutic agent as the fluid removes material.

The devices illustrated in FIGS. 13 and 14 provide a method for designing and constructing devices and systems that resemble a sandwich structure. Such devices may be manufactured by a number of planar processes. These processes include micro-embossing, optical lithography, laser cutting, machining, and injection molding. The 2-D nature of the device also simplifies diffusion calculations. This provides a convenient way to design and fabricate a device for any specific application. A flow diagram depicted in FIG. 15 provides an exemplary process for manufacturing such devices.

Figure 15:
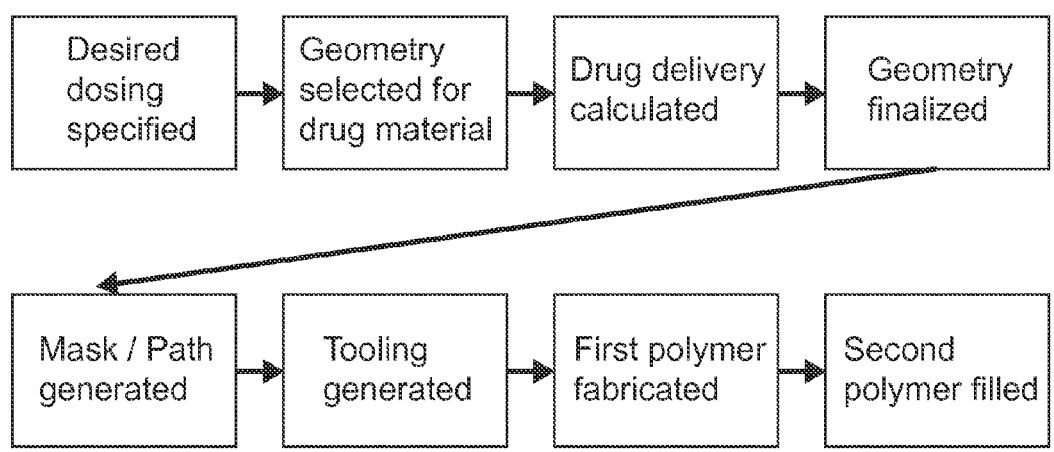
FIG. 15 depicts a flow diagram providing an exemplary process for computer-aided design of a device or system provided herein.

Referring to FIG. 15, a therapeutic agent dosing profile is first specified. Initial geometries are selected by computer, then simulated using finite element analysis. The flat shape and axial symmetry of the device lends itself to fast analysis by the computer. Following this, the computer optionally selects new geometries and re-simulates the dosing profile. The process is optionally repeated iteratively until a geometry is identified that can produce the desired dosing profile. The 2-D geometry is converted into cutting paths or a mask for fabrication purposes. Using standard lithography and micro-machining or other precision manufacturing tools, a mold or die is generated from the cutting path or mask. Alternatively, the cutting path is used with a cutting tool to directly cut, burn, ablate, or otherwise remove material that is placed on a flat surface. After the first material is fabricated, a second material is cast or embossed into the first, filling all open spaces. The device is capped on top and bottom, producing a 2-D sandwich of material. The caps are non-permeable material, so when placed in an aqueous environment, the material will degrade and produce the therapeutic agent profile predicted by the simulation. Although this same design and manufacturing process can be done for 3-D devices, we anticipate that the 2-D embodiment is significantly easier to manufacture since many manufacturing tools are available that can produce arbitrary 2-D shapes in materials.

These embodiments are meant to be illustrative examples and not exhaustive of the types of useful devices that can be built by patterning membranes over chambers containing expandable materials or by patterning two or more degradable materials near each other. The device and method discussed above will have great utility for a variety of applications including, but not limited to: (1) controlled, sustained and programmable therapeutic agent delivery, (2) controlled, sustained and programmable chemical treatments (e.g., for batch growth) (3) controlled, sustained and programmable food delivery (e.g., for aquariums and other aqueous environments).

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for controlled release of one or more active ingredients, the device comprising:
   a) at least two release apertures, each release aperture operably associated with a deflectable member comprising a rupturable membrane and/or a deflectable cap;
   b) a base comprising a porous membrane layer, and a non-porous substrate layer in contact with the porous membrane layer; and
   c) at least two chambers, each chamber juxtaposed between a respective one of the release apertures and the porous membrane layer, each chamber containing a matrix comprising one or more active ingredients and an agent that expands when contacted with an aqueous solution,
   wherein the non-porous substrate layer comprises a plurality of channels configured with at least two pre-determined patterns, each pre-determined pattern adapted for fluid communication with a respective one of the chambers, and wherein each channel of the plurality of channels is suitable for contacting the porous membrane layer with an aqueous solution,
   wherein the device is suitable for implantation in a biological system.

2. The device of claim 1, wherein the cap is comprised of polymer, wax or gel.

3. The device of claim 1, wherein the one or more active ingredients comprises a plurality of active ingredients.

4. The device of claim 3, wherein each active ingredient is released according to a specific release profile.

5. The device of claim 1, wherein the one or more active ingredients is a pharmaceutical compound.

6. The device of claim 1, wherein the agent is a polymer.

7. The device of claim 6, wherein the polymer is polylactic-co-glycolic acid (PLGA).

8. The device of claim 1, wherein the matrix further comprises hydrophilic binders, aqueous solution-soluble diluents, surfactants, lubricants, disintegrants, antioxidants, or non-aqueous solution-soluble diluents, or any combination thereof.

9. The device of claim 1, wherein the biological system is an ocular system.

10. A device for controlled release of one or more active ingredients, the device comprising:
    a) at least two release apertures, each release aperture operably associated with a deflectable member comprising a rupturable membrane, the rupturable membranes comprising variable thickness configured with at least two predetermined patterns;
    b) a base comprising a porous membrane layer; and
    c) at least two chambers, each chamber juxtaposed between a respective one of the release apertures and the porous membrane layer, each chamber containing a matrix comprising
    one or more active ingredients and
    an agent that expands when contacted with an aqueous solution,
    wherein each of the at least two predetermined patterns is adapted for fluid communication with a respective one of the chambers, and
    wherein the device is suitable for implantation in a biological system.

11. A system comprising a plurality of devices as set forth in claim 1 or claim 10 arrayed in a housing, wherein each device in the system comprises the same or different active ingredient and wherein each device in the system comprises the same or different release kinetics of the active ingredient.

* * * * *